US011878099B2

(12) United States Patent
Keller et al.

(10) Patent No.: US 11,878,099 B2
(45) Date of Patent: Jan. 23, 2024

(54) APPARATUS AND METHOD FOR PREPARING A DIALYSIS SOLUTION

(71) Applicant: Fresenius Medical Care Deutschland GmbH, Bad Homburg (DE)

(72) Inventors: Torsten Keller, St. Wendel (DE); Stefan Konrad Marterstock, Dettelbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 533 days.

(21) Appl. No.: 17/264,389

(22) PCT Filed: Jul. 30, 2019

(86) PCT No.: PCT/EP2019/070415
§ 371 (c)(1),
(2) Date: Jan. 29, 2021

(87) PCT Pub. No.: WO2020/025567
PCT Pub. Date: Feb. 6, 2020

(65) Prior Publication Data
US 2021/0299341 A1 Sep. 30, 2021

(30) Foreign Application Priority Data

Jul. 31, 2018 (DE) ...................... 10 2018 118 564.2

(51) Int. Cl.
*A61M 1/16* (2006.01)
*A61M 1/36* (2006.01)
*A61M 1/26* (2006.01)
(52) U.S. Cl.
CPC .......... *A61M 1/1672* (2014.02); *A61M 1/267* (2014.02); *A61M 1/3624* (2013.01);
(Continued)

(58) Field of Classification Search
CPC .. A61M 1/1672; A61M 1/1696; A61M 1/267; A61M 1/3624; A61M 2205/3327; A61M 2205/3389
See application file for complete search history.

(56) References Cited

U.S. PATENT DOCUMENTS

| 10,773,214 B2 * | 9/2020 | Nosrati ............... B01D 63/085 |
| 2011/0017665 A1 | 1/2011 | Updyke et al. |
| 2017/0065762 A1 | 3/2017 | Larsen et al. |

FOREIGN PATENT DOCUMENTS

| WO | WO-2009083011 A2 * | 7/2009 | .......... A61M 1/1696 |
| WO | WO2014/128293 | 8/2014 | |
| WO | WO2015/124716 | 8/2015 | |

* cited by examiner

*Primary Examiner* — Terry K Cecil
(74) *Attorney, Agent, or Firm* — Jacobson Holman PLLC

(57) ABSTRACT

The present invention relates to a method and to an apparatus for preparing a dialysis solution, wherein the apparatus has a first circuit and a second circuit, wherein the first circuit has a container for receiving the consumed dialysis solution or fresh water or another fluid, the primary side of a filter connected downstream of the container, and a return line from the primary side of the filter into the container, wherein the filter is configured to prepare purified water from the consumed dialysis solution or from fresh water or from another fluid, and wherein the second circuit has the secondary side of the filter, the dialyzate side of a dialyzer, a reservoir, a line that leads from the reservoir to the secondary side of the filter, by means of which dialyzate or a dialyzate concentrate can be supplied to the secondary side of the filter, and a filtrate line that leads away from the secondary side of the filter.

21 Claims, 3 Drawing Sheets

(52) U.S. Cl.
CPC ............... *A61M 2205/3327* (2013.01); *A61M 2205/3389* (2013.01)

APPARATUS AND METHOD FOR PREPARING A DIALYSIS SOLUTION

FIELD OF INVENTION

The present invention relates to an apparatus and to a method for preparing a dialysis solution.

BACKGROUND OF INVENTION

It is known from the prior art to supply dialysis machines with a ready-to-use dialysis solution from e.g. a line system that is connected to a central device for preparing the dialysis solution and that is generally configured to supply a plurality of dialysis machines with dialysis solution. Alternatively to this, there is the option of preparing the dialysis solution at the dialysis machine itself, i.e. decentrally. An RO system (RO=reverse osmosis) that is part of the dialysis machine or that can be designed as a separate unit can be provided for this purpose for the preparation of ultrapure water. The ultrapure water is mixed with one or more concentrates in the dialysis machine to obtain a ready-to-use dialysis solution for the treatment of the patient.

The large water requirements required for this kind of preparation of the dialysis solution has the result that known dialysis machines require an additional RO system so that the total systems are comparatively large and heavy and a transport of the equipment is only possible with difficulty. This disadvantage plays a particular role, for example, in home hemodialysis and with portable units that are intended to allow the patient mobility during the treatment.

RELATED INVENTION

FIG. 5 shows a conceivable possibility not covered by the present invention of an embodiment of a dialysis machine in which the water consumption is reduced in that new, i.e. read-to-use dialysis fluid is acquired while using consumed dialysis fluid, which produces a reduction in water consumption.

The inlet for fresh water into the container 10 is marked by reference numeral I, with the inlet line being blockable by a valve V1. The drain from the container 10 for consumed solution is marked by O, with the drain line being blockable by a valve V2. The container 10 will also be called a water inlet chamber in the following. A container 10 having a stationary water connection or also any other container such as a bag such as a dialyzate bag can generally be used with a stationary water connection. The container 10 can have rigid or flexible walls.

Reference numeral 100 marks a dialyzer that preferably has a plurality of membranes, preferably a membrane bundle, that are flowed through by dialyzate on one side D and by blood on the other side B. The dialysis solution that has flowed through the dialyzer 100 and is thus charged with contaminants from the blood is called a consumed dialysis solution or consumed dialyzate. The consumed dialyzate that is conducted from the dialyzer 100 through the line 40 back into the water inlet chamber 10 is sucked in by a pump 50 and is pumped into a circuit which is positioned upstream and which is a first circuit.

This circuit substantially comprises the pump 50, the container 10, the primary side of the filter 20, i.e. the section in front of the filter membrane or in front of another filter medium, and the pressure relief valve 60 including the lines connecting these components. Reference numeral 30 designates the return line from the pressure relief valve 60 to the container 10.

The pump 50 conveys the consumed dialysis solution from the container 10 to the primary side 21 of the filter 20 and conveys the retentate via the valve 60 back into the container 10. A pressure drop arises over the valve 60 here and thus also a pressure on the filter 20. This pressure or pressure drop can be set by the valve 60 and can thus be coordinated with the ideal working point of the filter 20.

The pressure gradient between the primary side 21 and the secondary side 22 of the filter 20 has the result that a flow takes place through the filter membrane or through the other filter medium, with the filtrate being present in the form of ultrapure water on the secondary side 22, i.e. after the filter medium. It enters into the mixing device 200 that can be designed as a mixing circuit, a mixing container, a line section, etc.

The mixing of the ultrapure water with one or more concentrates such as with a base concentrate and an acid concentrate takes place in the mixing circuit or mixing container 200, etc. The heating or post-heating of the dialysis solution can also take place there so that, where possible, no heat is withdrawn from the blood in the dialyzer 100 by the dialysis solution. A second circuit thus comprises the secondary side 22 of the filter 20, the mixing device 200, the dialyzate side D of the dialyzer 100, and a line system connecting these components, with a line leading from the dialyzate side D of the dialyzer 100 back into the water inlet chamber 10.

As can be seen from FIG. 5, the first and second circuits are two closed, cascaded water circuits or liquid circuits. More than two of these circuits can generally also be present.

The filter 20 can optionally be based on a graphene filter technique, whereby the ultrapure water can, for example, be simultaneously separated from the filter without dissolved oxygen. This saves further components in the dialysis machine such as a separate degassing circuit.

A high performance can be achieved by the "washing" of the filter 20 at its primary side 21 via the valve 60 and the contamination of the filter 20 can be prevented or delayed. The service life of the filter 20 is thereby increased. The filter 20 can additionally be flushed free in that the valve 90 short circuits the pressure relief valve 60. In this case, the liquid moves into the bypass that includes the valve 90 while bypassing the valve 60 and moves from there back into the container.

As can further be seen from FIG. 5, a filling level sensor 110 is located in the container 10. If this reports that the filling level in the container 10 has fallen below a limit value, a conclusion can be drawn on a leak since both the first circuit and the second circuit are closed and the filling level would thus have to remain the same. The valves V1 and V2 are closed in normal operation, i.e. when no change of water takes place.

The presence of a conductivity cell 70 after, i.e. downstream, of the pump 50 further results from FIG. 5. The concentration of the contaminated liquid caused by the circuit operation is thus measurable and when the water in the circuit should be completely replaced (fresh water cycling) can be derived. This exchange can take place by using the valves V1 and V2 and can be volumetrically balanced with the aid of the level sensor 110 in the container 10. In normal dialysis operation, the valves V1 and V2 are closed, whereby the level sensor 10 can also be used, as stated, as leak monitoring. If one of the two closed circuits loses liquid, this is detectable with reference to the level in the container 10. This serves patient safety.

The function of the filter 20 can be monitored by a further conductivity cell 80 after, i.e. downstream of, the filter 20. As soon as relevant damage to the filter membrane or to another filter medium is present, conductive ions pass through the filter 20 that can in turn be detected by the sensor 80. Optionally, the transmembrane pressure can be monitored over the filter 20 by means of the pressure sensor 102 arranged downstream of the filter 20 to be able to determine a degradation or loss of performance of the filter.

Since the two circuits are closed, the energy requirements for the heating of the dialyzate falls considerably. As a consequence, smaller heating devices can be used than is the case with machines known from the prior art. A heat exchanger is admittedly optionally still conceivable for the fresh water cycling, but can also be dispensed with for cost reasons. As stated above, the ultrapure water arising at the secondary side 22 of the filter 20 moves into the mixing part 200 of the machine and is there e.g. enriched with bicarbonate and acid so that a ready-to-use dialysis liquid is available at the dialyzer 100 for exchange with the blood of the patient. Reference symbol B/U marks the balancing unit and/or an ultrafiltration pump that withdraws a partial volume from the consumed dialysis liquid corresponding to the prescription by the physician.

Toxic substances that are larger than water can still be removed from the patient by the two-stage (cascaded) filter approach. These substances, also including ions such as Na and Cl from the dialysis liquid are subsequently concentrated in the container 10 and are discarded via the outflow O as part of the fresh water cycling. The ultrafiltration still e.g. takes place via a UF pump in the unit B/U that conveys directly into the drain. Since the circuits are closed circuits, the advantages of volumetric balancing such as today, for example, takes place with the aid of a balancing chamber can be maintained.

The requirement for additional degassing measures/degassing apparatus is dispensed with in this design due to the properties of the filter 20 to be impermeable for gases. Alternatively, if required, depending on the filter used, a degassing restrictor/degassing apparatus can also be introduced into the upstream circuit, i.e. the first circuit, such as is shown by reference symbol E in FIG. 5. A separate chamber that can, for example, be arranged between 20 and 60 in FIG. 5 can, however, also serve as an air separation chamber.

It is pointed out at this point that all the features explained with respect to FIG. 5 can be the subject matter of the present invention individually or also in combination. It is further pointed out that the same reference numerals in FIG. 5 and in FIGS. 1 to 4 characterize elements that are the same or have the same function.

The arrangement in accordance with FIG. 5 suffers from the disadvantage that a concentration of the solution located in the container 10 takes place over the course of time. A solution that is increasingly more concentrated over the course of the treatment is thus also present at the primary side 21 of the filter 20. The osmotic pressure produced by this solution makes the filtration in the filter 20 more difficult since it counteracts the formation of filtrate. As the concentration on the primary side 21 increases, an increasing pressure generated by the pump 50 therefore becomes necessary to obtain a sufficient amount of ultrapure water on the secondary side 22 of the filter 20.

SUMMARY OF INVENTION

It is the underlying object of the present invention to provide an apparatus with which an efficient ultrapure water acquisition is possible.

This object is achieved by an apparatus having the features of claim 1.

Provision is accordingly made that the apparatus for preparing a dialysis solution has a first circuit and a second circuit, wherein the first circuit has a container for receiving the consumed dialysis solution or fresh water or another fluid, the primary side of a filter connected downstream of the container, and a return line from the primary side of the filter into the container, wherein the filter is configured to prepare purified water from the consumed dialysis solution or from fresh water or from another fluid, and wherein the second circuit has the secondary side of the filter, the dialyzate side of a dialyzer, a reservoir, a line that leads from the reservoir to the secondary side of the filter, that will also be called a concentrate line in the following, and by means of which dialyzate or a dialyzate concentrate can be supplied to the secondary side of the filter, and a filtrate line that leads away from the secondary side of the filter.

Provision is made in accordance with an embodiment that the reservoir receives concentrates such as a bicarbonate concentrate or an acid concentrate or a ready-to-use dialysis solution or a mixture of a base concentrate, in particular a bicarbonate concentrate, and an acid concentrate.

Unlike the arrangement visible from FIG. 5, a solution either in the form of a ready-to-use dialysis solution or preferably in the form of a liquid concentrate is supplied to the secondary side of the filter. This has the advantage that the osmotic pressure gradient reduces correspondingly over the filter membrane and a more efficient preparation of filtrate is thus possible.

The concentrate that is supplied to the secondary side of the filter is preferably a concentrate that is required for the preparation of the dialysis solution and is particularly preferably a concentrate containing bicarbonate. It is particularly preferred if the concentrate contains only a single conductive component such as bicarbonate apart from water and optionally common salt.

The filter has the object of preparing purified water from the solution contained in the container, i.e. water whose content or concentration of contaminants and other ingredients such as ions or molecules is smaller than in the solution supplied to the filter. The filter is preferably configured to prepare ultrapure water, which is understood within the framework of the present invention as water that is suitable to be used for preparing a ready-to-use dialysis solution. The filter can be in one or multiple stages, with the plurality of stages being flowed through by solution one after the other. The use of a plurality of filters connected in series is also conceivable to obtain the desired degree of purity of the water. The filter is preferably a hollow fiber module or a wound module such as is used for RO (reverse osmosis) or FO (forward osmosis) processes.

Said filter is preferably a graphene filter. A filter is understood by this that contains graphene or a graphene derivative such as graphene oxide as the filter material or whose filter material consists of or comprises these materials. Graphene or graphene oxide is gas-tight, but simultaneously water-permeable, which brings about the advantage within the framework of the present invention that a gas entry does not take place from the first into the second circuit and thus into the ready-to-use dialysis solution. The present invention is, however, not restricted to these filters, but rather also comprises other filters that are preferably impermeable for gas, but allow liquid to pass. If the filter used does not have the property of impermeability for gas, air can, for example, be separated at the primary side by a degassing restrictor and can then be conveyed via a valve (preferably a pressure-restricting valve) back into the container and can thus be removed. Other degassing procedures are also possible.

The filter preferably has four connectors of which two are provided at the primary side and two at the secondary side.

In a preferred embodiment of the invention, a return line from the dialyzate side of the dialyzer into the container is present by which consumed dialysis solution is supplied to the container. Provision can be made alternatively to this that a return line from the dialyzate side of the dialyzer into a drain is present, i.e. the consumed dialysis solution is discarded.

The filtrate line that leads away from the secondary side of the filter can connect the secondary side of the filter to a balancing chamber of the apparatus. In this case, the filtrate, preferably ultrapure water, that is acquired through the filter is e.g. mixed with the concentrate and this mixture is supplied to the balancing chamber of the dialysis machine. If the concentrate is a bicarbonate solution, a bicarbonate solution diluted by the ultrapure water is thus supplied to the balancing chamber. In a further step, the acid concentrate can then be supplied to this mixture or the diluted bicarbonate solution, etc. can be filled into a container such as into the reservoir in which a defined quantity of further concentrate or of other components required for the ready-to-use dialysis solution is present.

Provision can be made in a further embodiment that a concentrate comprising the acid concentrate and the base concentrate is supplied directly to the filtrate side of the filter. The concentrate solution of this embodiment effects a particularly favorable filtration performance of the filter. The dialyzate concentrate in accordance with this embodiment comprises both a base concentrate, in particular a base concentrate, and an acid concentrate.

It is also conceivable that the filtrate line is in fluid communication with the reservoir so that e.g. the filtrate acquired by the filter, preferably ultrapure water, is e.g. mixed with the concentrate and this mixture is supplied to the reservoir of the dialysis machine. The reservoir or the mixing chamber is preferably connected downstream of the balancing chamber.

It is furthermore conceivable that ready-to-use dialysis solution or a concentrate, in particular a bicarbonate concentrate, is present in the reservoir that is used to prepare a ready-to-use dialysis solution.

The reservoir is preferably a dialyzate mixing device in which the ready-to-use dialysis solution is mixed and is supplied from there to the dialyzate side of the dialyzer.

A pump is preferably located in the concentrate line and is configured to supply a defined volume or a defined volume flow to the secondary side of the filter. The pump can, for example, be a volumetric pump or an eccentric membrane pump. It is possible in this manner to implement a purely volume-controlled mixing process that can, for example, be monitored by an independent conductivity measurement.

Provision can furthermore be made that a pump is arranged in the first circuit, preferably upstream of the primary side of the filter, to effect a flow of the fluid in the first circuit. This pump conveys the fluid located in the container to the primary side of the filter.

Alternatively or additionally, a pressure relief device can be provided in the first circuit, preferably downstream of the filter, by means of which the pressure on the primary side of the filter can be set.

One or more sensors, preferably one or more conductivity measuring cells, that are arranged upstream and downstream of the primary side of the filter can be arranged in the first circuit to monitor the process or to control the process carried out by means of the apparatus. Alternatively or additionally, one or more sensors, preferably one or more conductivity measuring cells, can be arranged in the second circuit in the concentrate line and/or in the filtrate line.

Provision can furthermore be made that one or more pressure measuring devices are arranged downstream of the secondary side of the filter and/or upstream of the primary side of the filter. In this manner, a statement can be made on the pressure conditions in the respective circuit and also on transmembrane pressure over the filter membrane.

The apparatus can furthermore have an ultrafiltrate pump for leading off dialysis solution, preferably from the return line from the dialyzer to the container and/or a balancing chamber for the balanced supply and leading off of dialysis solution to and from the dialyzer.

The first and/or second circuits can be closed or open. "Open" is to be understood to mean that no circuit is present in the more restricted sense, but rather a fluid system that has a drainage line at at least one point by means of which a fluid can be led out of the circuit and discarded.

The container can be formed as a bag, in particular as a flexible bag, further particularly as a disposable article.

The claimed apparatus can be a dialysis machine or a part of a dialysis machine or an apparatus for mixing dialysis solution.

The present invention further relates to a method of manufacturing a dialysis solution using an apparatus in accordance with the invention, wherein the solution is supplied from the container to the primary side of the filter and the retentate is led back into the container, and wherein a dialysis solution or a dialyzate concentrate is supplied to the secondary side of the filter and is mixed with the permeate of the filter on its secondary side.

The dialysis solution or a dialyzate concentrate supplied to the secondary side of the filter is preferably led out of said reservoir and is conducted to the secondary side of the filter.

A pump can be arranged in the concentrate line, which pump supplies a defined volume or a defined volume flow of dialysis solution or of dialyzate concentrate to the secondary side of the filter.

Provision can furthermore be made that the permeate arising on the secondary side of the filter is conducted together with the supplied dialysis solution or dialyzate concentrate into the reservoir and/or into a balancing chamber.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment shown in the drawing.

BRIEF DESCRIPTION OF THE DRAWINGS

There are shown.

DETAILED DESCRIPTION OF THE DRAWINGS

Figure 4:
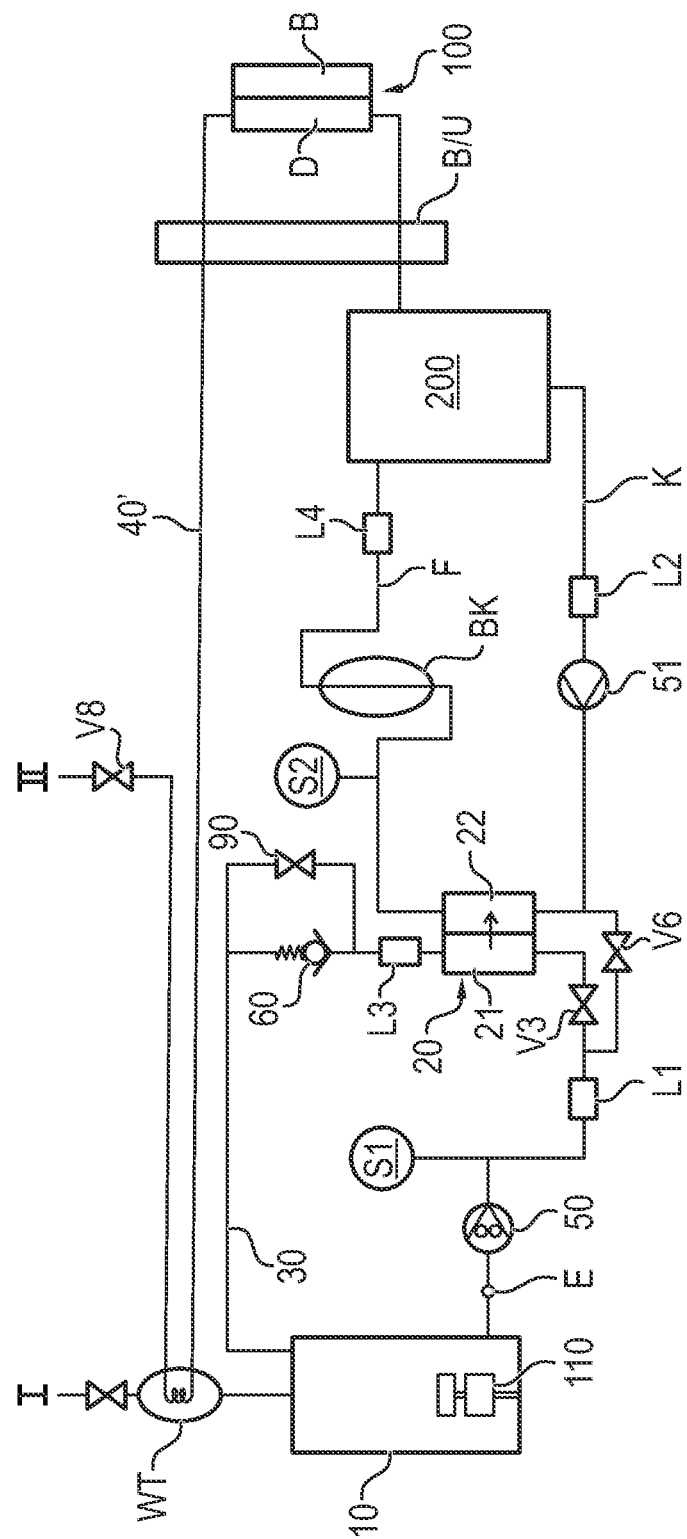
FIG. 4: a schematic flowchart of an apparatus in accordance with the invention in a fourth embodiment of the invention.
Figure 5:
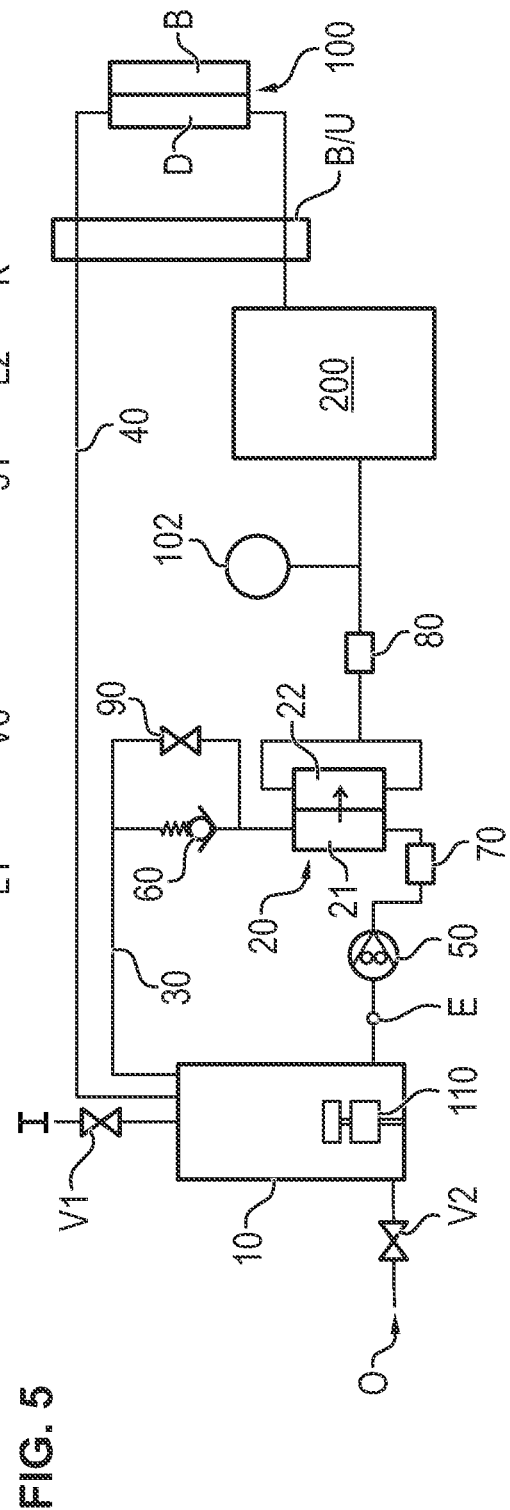
FIG. 5: a schematic flow diagram of a further apparatus that is not a subject of the invention.

As stated above, FIG. 5 shows a variant that is not the subject of the invention. Elements that are the same or are functionally the same in accordance with FIG. 5 have the same reference numerals as in FIGS. 1 to 4 so that reference is also made to FIG. 5 with respect to the structure of the apparatus shown in FIGS. 1 to 4.

Figure 1:
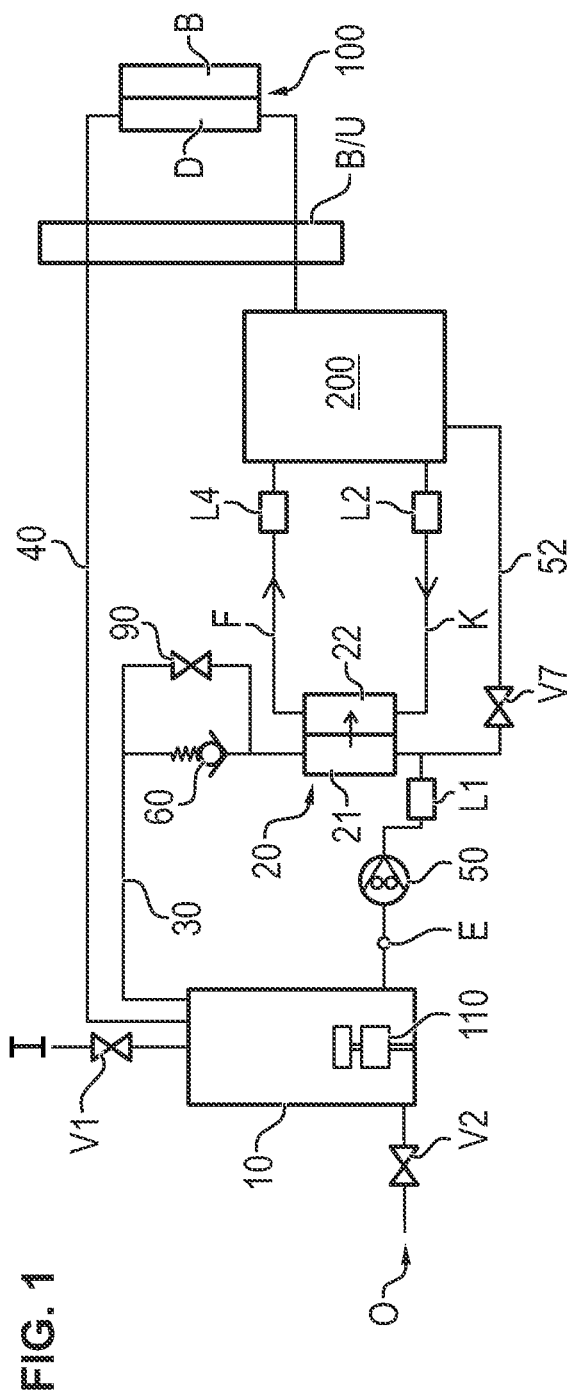
FIG. 1: a schematic flowchart of an apparatus in accordance with the invention in a first embodiment of the invention.

As can be seen from FIG. 1, the apparatus shown in FIG. 1 essentially differs with respect to the arrangement in accordance with FIG. 5 in that a line K runs from the reservoir 200 to the secondary side 22 of the filter, through which line K the ready-to-use dialysis solution flows. The conductivity sensor L2 is located in this line K.

At the drain side, a filtrate line F leads from the secondary side 22 of the filter 20 to the reservoir 200. This line conducts a mixture of the dialyzate supplied over the line K with the ultrapure water acquired by means of the filter 20, e.g. by RO. The conductivity sensor L4 is located in the line F.

A line 52 is furthermore provided that can be closed by the valve V7 and by which the reservoir 200 is in fluid communication with the line through which fluid is supplied from the container to the primary side 21 of the filter 20. The pump 50 and the conductivity sensor L1 are located in the last-named line. The reservoir 200 is accordingly in fluid communication with the primary side 21 of the filter 20 with an open valve.

Figure 2:
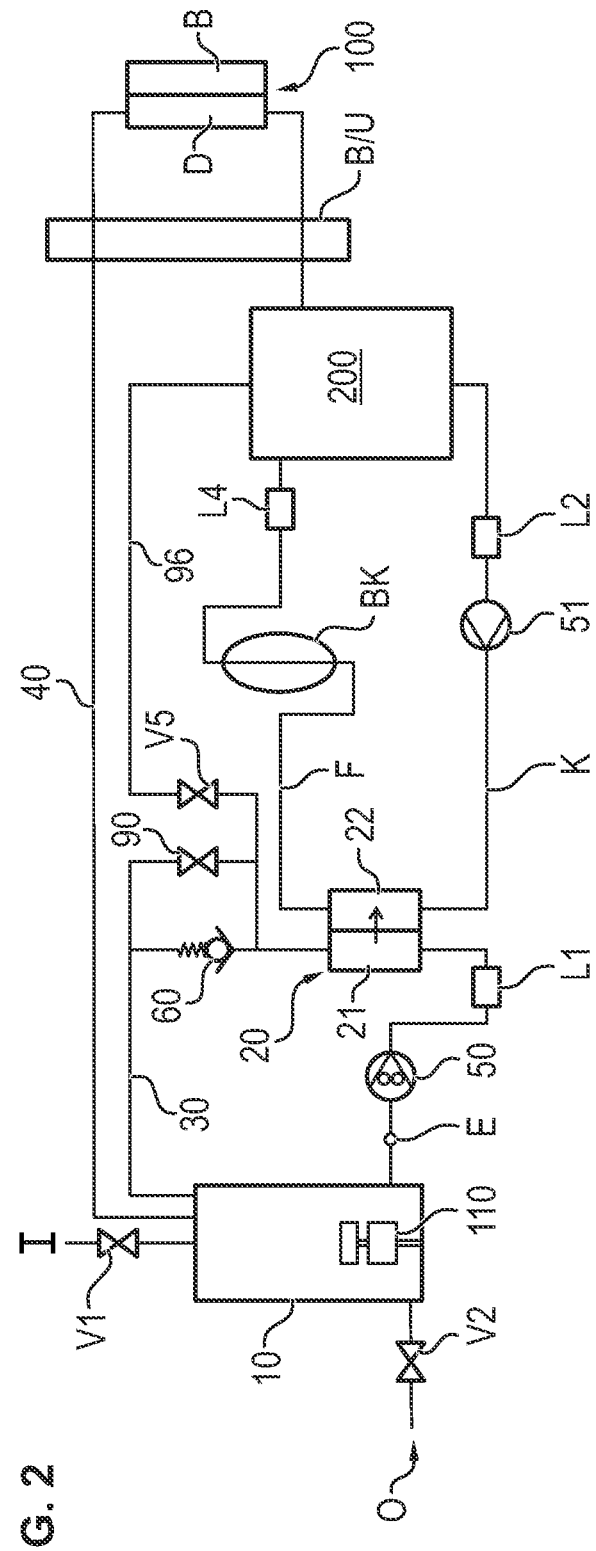
FIG. 2: a schematic flowchart of an apparatus in accordance with the invention in a second embodiment of the invention.

In an apparatus in accordance with FIG. 1, the mass transfer or the volume transition over the filter is measured and ensured by the conductivity sensors L2 and L4. FIG. 2 shows an embodiment in which a concentrate or a concentrate mixture, in particular a bicarbonate concentrate, is conveyed through the line K. The pump 51 located in the line K serves this purpose. A concentrated solution is thus conveyed to the secondary side 22 of the filter, with its conductivity being determined by the conductivity sensor L2. A certain, i.e. defined, volume of this concentrate or of the mixture is conveyed by means of the pump 51. This concentrate or mixture is mixed with ultrapure water in the filter 20, which ultrapure water dilutes the concentrate or the concentrate mixture on the secondary side.

The mixture is supplied to the balancing chamber BK that is designed with four valves and that has two chambers which are separated by a movable partition wall and of which each has an inflow valve and an outflow valve.

The balancing chamber BK thus receives the concentrate or concentrate mixture diluted with ultrapure water. A purely volume controlled mixing process thus results that can be monitored by an independent conductivity measurement (conductivity sensor L4). Only the concentrate contributes to the conductivity (in contrast to the embodiment in accordance with FIG. 1) as a component of the ready-to-use dialysis solution. An expected value for the conductivity can thus be calculated. The regulation to an expected value of a conductivity can be simply carried out.

It is also conceivable to provide a regulation or a feedback loop whose desired value is the volume of diluted concentrate/concentrate mixture supplied to the balancing chamber, with the actual value being provided by the conductivity measurement. The specific retention capability of the filter is decisive for this. With knowledge of the conductivity in the line K and with knowledge of the conductivity in the line F, a determination can be made as to by which amount the volume conveyed by the pump has increased due to the transfer of ultrapure water, i.e. which volume is supplied to the balancing chamber or to the reservoir 200 connected downstream of it.

As can further be seen from FIG. 2, the primary side 21 of the filter 20 or the lines leading off therefrom is in fluid communication with the reservoir 200 via the line 96 in which the valve V5 is located.

Figure 3:
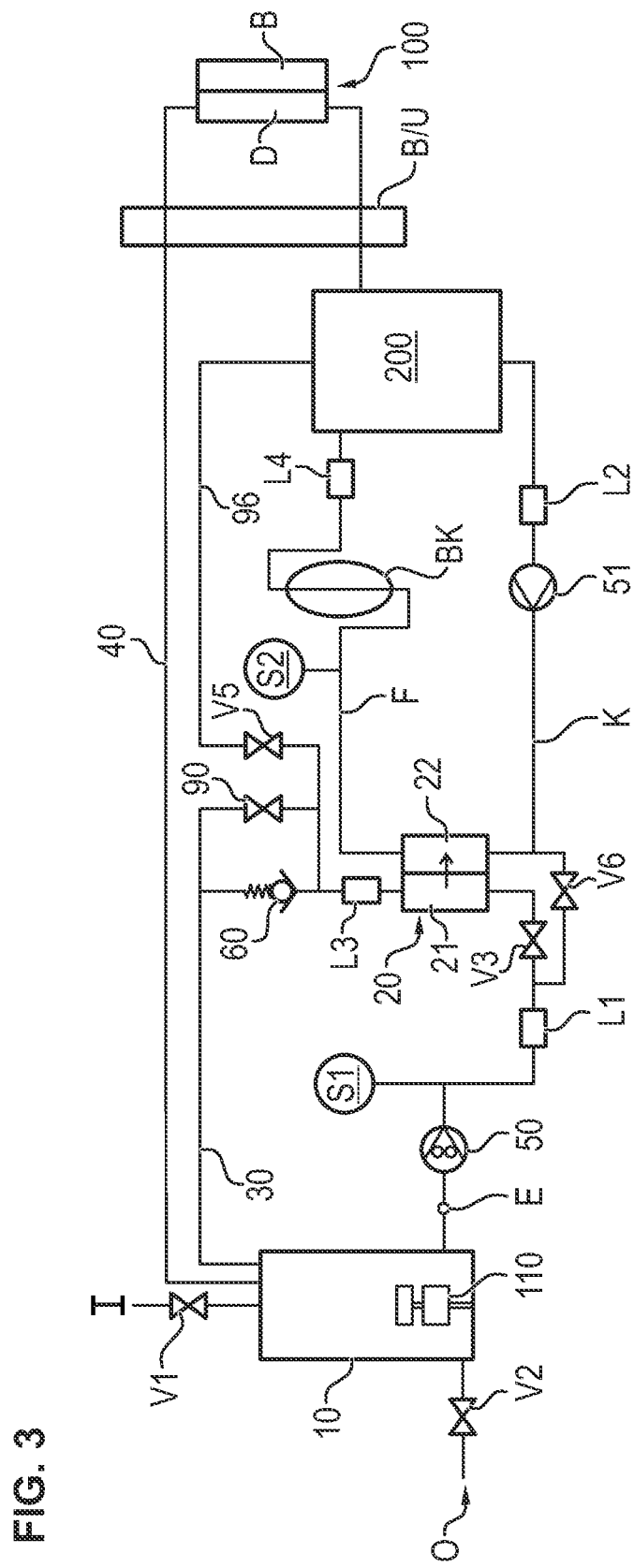
FIG. 3: a schematic flowchart of an apparatus in accordance with the invention in a third embodiment of the invention.

The embodiment in accordance with FIG. 3 differs from the variant in accordance with FIG. 2 by a total of four conductivity sensors L1-L4 of which two are arranged upstream and downstream of the primary side 21 of the filter and two are arranged in the concentrate line K and in the filtrate line F. With knowledge of the input conductivity and output conductivity, the process can additionally be verified, controlled, and monitored.

Pressure measurement sensors S1 and S2 are furthermore provided that serve the monitoring of the transmembrane pressure over the membrane of the filter 20. The sensor S1 is located at the inflow side on the primary side of the filter 20 and the sensor S2 is located in the filtrate line F. The values of the sensors can be used to be able to recognize a degradation of the filter F e.g. by scaling and to be able to plan and carry out flushing cycles/regeneration cycles of the filter.

It can additionally be recognized by means of the sensor S2 whether sufficient ultrapure water has flowed over the filter 20 onto its secondary side 22 and whether the balancing chamber is full so that the desired mixing relationship is reached and the balancing chamber can be switched over or cycled. A new "mixing cycle" can then be started by the pump 51.

Alternatively, the evaluation of the torque or of the motor current of the pump 51 can be used to reach the desired mixing ratio.

The value of the conductivity sensor L1 can be used to control the fresh water cycle, i.e. to recognize when the retentate in the container 10 has to be replaced by fresh water.

Not only the use of a filter 20 is generally covered by the invention, but rather also the use of a plurality of filters connected after one another, i.e. cascaded. This relieves the pump 50, but requires the presence of a plurality of pumps.

The chamber 10 can be designed as a rigid container or as a bag.

The filter 20 can be flushed and thus cleaned e.g. by opening the valves V3 and 90.

Alternatively, the secondary side can initially be filled with fresh water via the valve V5 or V6. A filling with fresh water via the filter 20 and the balancing chamber BK is, however, advantageous.

As can be seen from FIG. 4, the method can also be carried out without the return of consumed dialyzate into the container 10. In this case, the consumed dialyzate is discarded via the line 40'. A preheating of the water supplied to the container 10 by means of the consumed dialysis solution takes place via the heat exchanger WT.

The invention claimed is:

1. An apparatus for preparing a dialysis solution, wherein the apparatus comprises a first circuit and a second circuit, wherein the first circuit has a container (10) for receiving a consumed dialysis solution or fresh water or another fluid, a primary side (21) of a filter (20) connected downstream of the container (10), and a return line (30) from the primary side (21) of the filter (20) into the container (10), wherein the filter (20) is configured to prepare purified water from the consumed dialysis solution or from fresh water or from another fluid, and wherein the second circuit has a secondary side (22) of the filter (20), a dialyzate side of a dialyzer (100), a reservoir (200), a line (K) that leads from the reservoir (200) to the secondary side (22) of the filter and by means of which dialyzate or a dialyzate concentrate can be supplied to the secondary side (22) of the filter (20), and a filtrate line (F) that leads away from the secondary side (22) of the filter (20).

2. An apparatus in accordance with claim 1, further comprising a return line (40) from the dialyzate side of the dialyzer (100) into the container (10) or a line (41) from the dialyzate side of the dialyzer (100) into a drain.

3. An apparatus in accordance with claim 1, wherein the filter (20) is a graphene filter.

4. An apparatus in accordance with claim 1, wherein the filtrate line (F) leads from the secondary side (22) of the filter (20) to a balancing chamber (BK) of the apparatus and/or to the reservoir (200).

5. An apparatus in accordance with claim 1, wherein ready-to-use dialysis solution or a concentrate is present in the reservoir (200) that is used to prepare a ready-to-use dialysis solution.

6. An apparatus in accordance with claim 1, wherein the reservoir (200) is a dialyzate mixing device (200).

7. An apparatus in accordance with claim 1, wherein a pump (51) is arranged in the line (K) and is configured to supply a defined volume or a defined volume flow to the secondary side (22) of the filter (20).

8. An apparatus in accordance with claim 1, wherein a pump (50) is arranged in the first circuit upstream of the primary side (21) of the filter (20) to effect a flow of liquid in the first circuit; and/or a pressure relief valve (60) by means of which pressure can be set on the primary side (21) of the filter (20) is provided in the first circuit downstream of the filter (20).

9. An apparatus in accordance with claim 1, wherein conductivity measuring cells (L1, L3) are arranged in the first circuit, one or more upstream and one or more downstream of the primary side (21) of the filter (20); and/or one or more conductivity measuring cells (L2, L4) are arranged in the second circuit in the line (K) and/or in the filtrate line (F).

10. An apparatus in accordance with claim 1, wherein one or more pressure measuring sensors (S1, S2) are arranged downstream of the secondary side (22) of the filter (20) and/or upstream of the primary side (21) of the filter (20).

11. An apparatus in accordance with claim 1, wherein the apparatus has an ultrafiltrate pump for removing dialysis solution from a return line (40) from the dialyzer (100) to the container (10) and/or has a balancing chamber (B) for a balanced supply and removal of dialysis solution to and from the dialyzer (100).

12. An apparatus in accordance with claim 1, wherein the filter (20) is impermeable to gas; and/or in that the second circuit does not have a degassing device.

13. An apparatus in accordance with claim 1, wherein the first and/or second circuits are closed or open.

14. An apparatus in accordance with claim 1, wherein the container (10) is configured as a rigid vessel or as a flexible bag and/or the apparatus forms a dialysis machine or a part of a dialysis machine.

15. A method of preparing a dialysis solution using the apparatus in accordance with claim 1, comprising the steps of: supplying the dialysis solution from the container (10) to the primary side (21) of the filter (20); returning a retentate from the primary side into the container (10); and supplying the dialysis solution or a dialysis concentrate to the secondary side (22) of the filter (20) and mixing with a permeate of the filter (20) on the secondary side (22).

16. A method in accordance with claim 15, wherein the permeate is supplied together with the dialysis solution or the dialyzate concentrate to the reservoir (200) in which a ready-to-use dialysis solution is prepared that is supplied to the dialyzer (100).

17. A method in accordance with claim 16, wherein a mixing region (200) is formed by the reservoir (200).

18. A method in accordance with claim 15, wherein the dialyzate concentrate contains only one single conductive component apart from water.

19. A method in accordance with claim 15, wherein a pump (51) is arranged in the line (K) and supplies a defined volume or a defined volume flow of dialysis solution or of dialyzate concentrate to the secondary side (22) of the filter (20).

20. A method in accordance with claim 15, wherein permeate arising on the secondary side (22) of the filter (20) is conducted together with the supplied dialysis solution or dialyzate concentrate into a balancing chamber (BK).

21. A method in accordance with claim 15, wherein permeate arising on the secondary side (22) of the filter (20) is conducted together with the supplied dialysis solution or dialyzate concentrate into the reservoir (200) or into a mixing region (200).

* * * * *